(12) United States Patent
Schweizer

(10) Patent No.: US 10,418,132 B2
(45) Date of Patent: Sep. 17, 2019

(54) METHOD FOR CONNECTING A MOBILE OPERATOR TERMINAL TO A DEVICE TO BE OPERATED

(71) Applicant: SIEMENS HEALTHCARE GMBH, Erlangen (DE)

(72) Inventor: Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 248 days.

(21) Appl. No.: 15/506,788

(22) PCT Filed: Jul. 28, 2015

(86) PCT No.: PCT/EP2015/067229
§ 371 (c)(1),
(2) Date: Feb. 27, 2017

(87) PCT Pub. No.: WO2016/030106
PCT Pub. Date: Mar. 3, 2016

(65) Prior Publication Data
US 2017/0262602 A1    Sep. 14, 2017

(30) Foreign Application Priority Data
Aug. 26, 2014   (DE) ........................ 10 2014 216 887

(51) Int. Cl.
| G06F 15/16 | (2006.01) |
| G16H 40/63 | (2018.01) |
| H04W 76/14 | (2018.01) |
| G06F 19/00 | (2018.01) |
| G08C 17/02 | (2006.01) |
| G05B 19/12 | (2006.01) |

(52) U.S. Cl.
CPC ........... *G16H 40/63* (2018.01); *G05B 19/124* (2013.01); *G06F 19/3418* (2013.01);
(Continued)

(58) Field of Classification Search
CPC .... H04W 76/14; G06F 19/3418; G06F 19/00; G08C 17/02; G08C 2201/30;
(Continued)

(56) References Cited

U.S. PATENT DOCUMENTS

| 8,897,647 B2 | 11/2014 | Friese et al. | |
| 2010/0115609 A1* | 5/2010 | Spence ............... | G06F 19/3418 726/19 |

(Continued)

FOREIGN PATENT DOCUMENTS

| DE | 102011002426 A1 | 7/2012 |
| DE | 102011082066 A1 | 3/2013 |

(Continued)

*Primary Examiner* — Frantz B Jean
(74) *Attorney, Agent, or Firm* — Laurence Greenberg; Werner Stemer; Ralph Locher

(57) ABSTRACT

A method for connecting a mobile operator terminal to a device to be operated includes outputting a code using an output element associated with the device. The code is transmitted to the mobile operator terminal. At least one piece of information related to the device is determined by decoding the transmitted code using software installed on the mobile operator terminal. A connection from the mobile operator terminal to a control unit associated with the device is then established with the aid of the piece of information related to the device and a piece of information related to the mobile operator terminal is transmitted from the mobile operator terminal to the control unit associated with the device over the established connection. A mobile operator terminal, a device for medical diagnosis or therapy and a system including a mobile operator terminal and a device, are also provided.

14 Claims, 4 Drawing Sheets

(52) U.S. Cl.
CPC ............ *G08C 17/02* (2013.01); *H04W 76/14*
(2018.02); *G05B 2219/23189* (2013.01); *G08C
2201/20* (2013.01); *G08C 2201/30* (2013.01);
*G08C 2201/93* (2013.01)

(58) Field of Classification Search
CPC ............ G08C 2201/93; G08C 2201/20; G16H
40/63; G05B 2219/23189; G05B 19/124
USPC ........................................................ 709/227
See application file for complete search history.

(56) References Cited

U.S. PATENT DOCUMENTS

| | | | | |
|---|---|---|---|---|
| 2011/0197067 A1* | 8/2011 | Corndorf | ............. | H04L 9/0844 |
| | | | | 713/172 |
| 2012/0188112 A1 | 7/2012 | Beals et al. | | |
| 2013/0317753 A1* | 11/2013 | Kamen | ............... | G06F 19/3418 |
| | | | | 702/19 |
| 2015/0207626 A1* | 7/2015 | Neftel | .................... | G08C 17/02 |
| | | | | 713/168 |

FOREIGN PATENT DOCUMENTS

| | | | | |
|---|---|---|---|---|
| EP | 2336995 A2 * | 6/2011 | ............. | G08C 17/02 |
| EP | 2336995 A2 | 6/2011 | | |
| WO | 2004095316 A1 | 11/2004 | | |
| WO | 2007025879 A1 | 3/2007 | | |
| WO | WO-2007025879 A1 * | 3/2007 | ............. | G08C 17/02 |
| WO | 2015011624 A2 | 1/2015 | | |

* cited by examiner

METHOD FOR CONNECTING A MOBILE OPERATOR TERMINAL TO A DEVICE TO BE OPERATED

Method for connecting a mobile operator terminal to a device to be operated

BACKGROUND OF THE INVENTION

Field of the Invention

The invention relates to connecting a mobile operator terminal to a device to be operated, particularly a device for medical diagnostics or therapy.

Current medical devices, e.g. x-ray devices, presently have a multiplicity of functions and displays. For this reason, touch-screen-based operator terminals are increasingly used as primary man-machine interface in such devices. Due to the current developments in the field of consumer electronics, the wish increasingly occurs from the user side that it should be possible to connect "own" tablet PCs and Smartphones to medical devices (this trend is also called "BYOD", i.e. bring your own device), in order to operate certain functions by this means or to be able to display, e.g., image data thereon (e.g. to show them to a patient).

In the document DE 10 2011 082 066 A1, a method for producing a communication connection between two communication facilities is described. In this context, a source address is also conveyed if a Bluetooth interface is used.

The publication US 2012/0 188 112 A1 deals with a configuration of a remote control by using matrix codes.

The document WO 2004/095 316 A1 relates to initializing a data communication by means of recording an image.

In the document WO 2015/011 624 A2, a system and a method are described which are implemented by a personal area network (PAN) by means of acoustic data transmission.

For a manufacturer of medical devices, connecting unknown devices into its system represents a great challenge, among others due to permission and security subjects. DE 10 2011 002 426 A1 describes an approach how this problem can be solved. It is shown there how a server is provided in the medical device for the HMI GUI (human machine interface, graphical user interface) which, by streaming, supplies the operator device with image information (and possibly audio information) and itself receives the user inputs on the basis of which the GUI is correspondingly updated.

In this approach, there is one problem: the devices provided by the operator or user for connection have quite different screen resolutions and computing powers and the bandwidth of the available (often wireless) data connection is also not always equally large or known in advance. Some systems also have only so-called single-touch displays (rather an exception at present) or even a mouse/track pad (if the user wishes to connect, e.g., a PC or laptop). Other devices have a multi-touch screen with only two-finger detection and no full ten-finger multitouch functionality.

I.e., the server in the medical device must know various boundary parameters of the unknown operator (input) device to be connected in order to match the GUI to the given factors (resolution and screen size, screen aspect ratio, availability of a touch screen with the detection of a plurality of fingers, audio reproducibility, connection bandwidth, . . . ) correctly before the customer device can be connected.

In addition, the question arises how connecting an unknown operator device to a quite particular medical device can be performed efficiently (in this context, it is also called pairing of the operator device and of the medical device).

The invention has the object of implementing an efficient connection of a mobile operator terminal to a device.

SUMMARY OF THE INVENTION

According to the invention, connecting a mobile operator terminal to a device to be operated takes place with the aid of a code. The device to be operated is a device for medical diagnosis or therapy, e.g. an x-ray device (C arch, mammography device etc.), nuclear spin tomography, ultrasound device, etc. A mobile operator terminal should be understood to be an operator terminal which is relatively easily transportable and can be brought to operate the device, as needed, by an operator into an operating area of the device, i.e. an area from which a connection for controlling the device can be established with the device. The mobile operator terminal can preferably set up a wireless data connection for controlling the device. But it is also conceivable that a connection is made by means of cable. Examples of mobile operator terminals are laptops, tablet computers and Smartphones.

The code used according to the invention contains at least one piece of information related to the device which is needed for setting up a connection from the mobile operator terminal to a control unit assigned to the device. The code preferably contains all required access data for setting up the connection from the mobile operator terminal to a control unit assigned to the device.

The code is output by an output element assigned to the device. Here and in the text which follows, an element assigned to the device or a unit assigned to the device, respectively, is understood to be an element or a unit which is mounted directly on the device or on an apparatus provided dedicated for the device and required for operating the device (e.g. a control console spatially separate from the device and connected for controlling).

According to one embodiment, the code is a code which can be displayed optically. In this case, the output element can have the form of an optical display. According to a further development of this embodiment, an optical conveyance of the code to the mobile operator terminal takes place in that the code is displayed by means of the output element and a recording of the displayed code is made by means of a camera of the mobile operator terminal.

Another possibility consists of an acoustic code. In this embodiment, the output element can consist of a loudspeaker unit which generates an acoustic signal which, e.g., is recorded by a microphone of the mobile operator terminal. In this context, acoustic signal is meant to be a signal in the form of sound waves which is preferably outside the frequency range audible to the human ear.

It is preferably provided to be able to provide both an optical and an acoustic code in order to thus have as few restrictions as possible with respect to the usability of mobile operator terminals necessitated by their functionality.

According to the invention, the code output by the device is conveyed to the mobile operator terminal. Preferably, the conveyance occurs wirelessly (e.g. photographing or filming of an optically reproduced code or wireless transmission of acoustic or electromagnetic signals), but a transmission by means of a cable which, e.g., connects the mobile operator terminal and the device or the mobile operator terminal and a stationary operator terminal assigned to the device and is configured as needed, is also possible.

After transmission of the code, the at least one piece of information related to the device is determined by decoding the conveyed code by means of software installed on the mobile operator terminal. In the case of the software installed on the mobile operator terminal, by means of which the code is decoded, it can be, e.g., application software which is adapted for the device or for a device type or product type assigned to the device.

With the aid of the at least one piece of information related to the device, a connection for exchanging data or control information from the mobile operator terminal to a control unit assigned to the device is set up. In this context, it can be, but does not need to be a direct connection. The connection can comprise, e.g., also two or even more links or connection sections which may also be operated by means of different communication protocols. E.g., it is conceivable that a first connection section connects the mobile operator terminal and a transmitting/receiving unit assigned to the device (e.g. HMI server) while signals are exchanged between the transmitting/receiving unit and a control unit assigned to the device via a second connection section.

Via the connection set up, at least one piece of information related to the mobile operator terminal is conveyed with respect to its relevant system parameters from the mobile operator terminal to the control unit assigned to the device.

Using a mobile operator terminal, the relevant parameters or performance data of which are stored in the controller of the device, requires adaptations, as a rule. The invention described above allows efficiently to provide relevant information related to the mobile operator terminal to the controller of the device for adaptations.

According to a further development of the subject matter of the invention, as determined by the at least one piece of information related to the mobile operator terminal data required for the operation of the device by the mobile operator terminal are conveyed from the control unit assigned to the device to the mobile operator terminal. These data can be selected or adapted according to requirements of the mobile operator terminal (GUI provided there, computing power, memory, . . . ). Transmission occurs, for example, via a transmitting/receiving unit (e.g. HMI server) assigned to the device.

According to one embodiment of the subject matter of the invention, as determined by the at least one piece of information related to the mobile operator terminal and conveyed to the control unit assigned to the device, an assessment of the suitability of the mobile operator terminal for operating the device to be operated is carried out. This assessment is preferably performed by the control unit. If the mobile operator terminal is not suitable for operating the device, a corresponding return message can be sent to the operator (e.g. information output or displayed on the mobile operator terminal or a stationary display belonging to the device). In the case of a positive result of the check, the mobile operator terminal can be used for operating without or with output of information about its suitability.

The invention also comprises a mobile operator terminal which is designed for the connection according to the invention to a device to be operated, a device which is designed for such a mobile operator terminal to be connectable to it in a manner according to the invention and a system which comprises such a mobile operator terminal and such a device.

BRIEF DESCRIPTION OF THE SEVERAL VIEWS OF THE DRAWINGS

The invention will be explained in greater detail in the text which follows within the context of an exemplary embodiment, with reference to figures in which.

DESCRIPTION OF THE INVENTION

In DE 10 2011 002 426 A1 is described how a central HMI (human machine interface) server that can both handle the generation of the user interface and the processing of user interactions can be provided in a medical device. In this context, the server can supply one or more clients at the same time. In this case, it runs either on dedicated hardware or is part of a virtual machine (VM) which is implemented on a component frequently already present (e.g. image processor).

Figure 1:
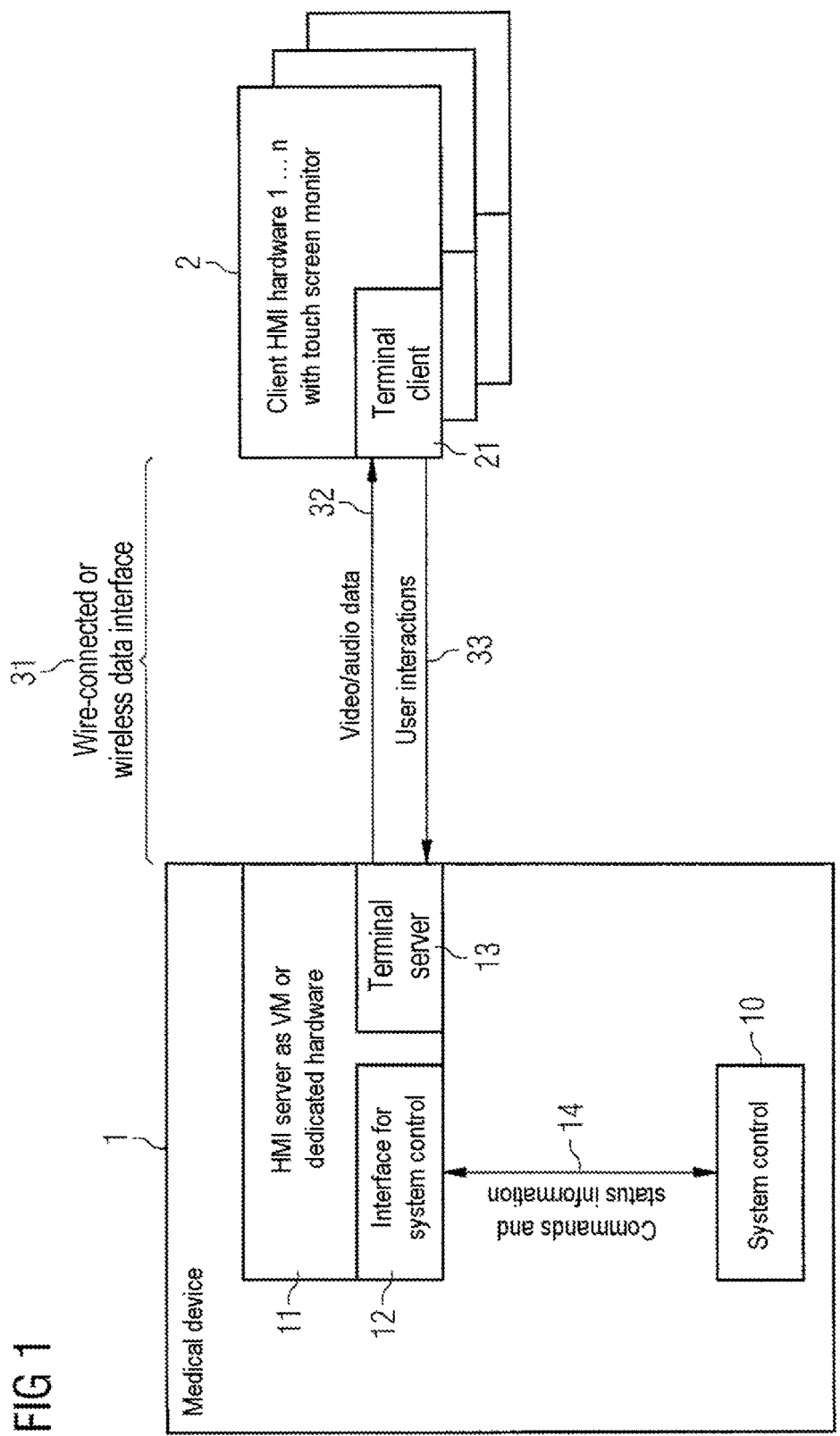
FIG. 1 shows a block diagram of an HMI server concept

The HMI server also has terminal server functionality which, depending on the transmission capacity of the data interface provided, allows it to stream video data (and possibly audio data) that is to say the actual GUI in compressed or uncompressed form to any client and on the return channel to report user interactions, that is to say, e.g., touch screen interactions (e.g. also multitouch gestures) of the user to the server which, in turn, converts them into commands to the system controller. This is shown in FIG. 1. The device 1 comprises a system controller 10 and an HMI server 11 which is designed as virtual machine or dedicated hardware. The HMI server 11 comprises an interface 12 for the system controller. Via this interface 12, commands and control information 14 are exchanged with the system controller 10. For the operation, hardware is used on which an HMI client 2 is installed. As indicated in FIG. 1, a plurality of HMI clients 2 or hardware units with HMI client 2 can be provided. Data and control information are conveyed between the HMI server 11 and HMI clients 2 by means of a terminal-server function unit 13 which is part of the HMI server, and a terminal-client function unit 21 which belongs to the HMI client 2.

Via a wire-connected or wireless interface 31, video or audio data are transmitted by the terminal server function unit 13 to the terminal-client function unit 21 (reference symbol 32). In the other direction (reference symbol 33), control information is conveyed by means of which user actions are triggered on the device 1. A terminal server protocol used is, for example, the RDP (remote desktop protocol) or VNC (virtual network computing) software.

In this process, the transmission proceeds in encrypted form secured by means of error correction in order to prevent misuse and errors. The technology of the data interface can here be varied, e.g., a network interface is available (also as wireless variant). It is only of importance that the available transmission capacity is adequate (for optimum results 10 MBit/s or more in the case of typical GUI resolutions) and the achievable latency period is sufficiently short, not to cause any noticeable delay between user interaction and reaction of the interface. Since the GUI software is not running locally on the client, the latter, apart from a minimum requirement for the screen resolution in order to be able to display the GUI completely, only needs to meet certain performance requirements and it is also not necessary to test and release any client hardware separately. The performance requirements essentially consist in that the client must be able to calculate quickly enough in order to decode the GUI in real time and to report back the operating interactions correspondingly. E.g., a performance criterion would be the minimum performance of the client or the availability of certain video decoding HW units (which all have current SoCs (system-on-a-chip) today) when the video stream from the HMI server is supplied, for example coded with the H.264 standard. As a rule, the Smartphone processors do not manage the decoding without loss of quality without the support of dedicated HW decoders.

Nevertheless, not every GUI is suitable. In addition, the data should be transmitted in a form to be processed well for the client hardware or software, respectively. This is where the present application comes into play.

It is proposed that on a medical device, after being manually triggered by the user or automatically after detection, e.g., of new or known WLAN devices or device classes (detection, e.g., via MAC address or media access control address within range of the medical device), a code, e.g. a matrix code is displayed, e.g., on one of the monitors of the medical device. Other optically functioning output elements (e.g. LEDs) are also possible. This code contains all necessary data in order to be able to access the medical device from a mobile operator terminal, e.g. by WLAN, i.e., e.g., WLAN SSID (service set identifier) and WLAN access password and preferred IP addresses incl. subnetwork mask. Furthermore, however, other information such as license information (enabling particular features) and time limits on the connection (e.g. a sequence timer for 6 hours) can also be present in the code.

On the mobile operator terminal, a generic App or application software, respectively (streaming client) by the medical device manufacturer is installed which does not need any specific device adaptation by the manufacturer of the medical device—comparable to a generic remote desktop client. This App can additionally read out the camera, present in most cases, of the mobile operator terminal (especially in the case of Smartphones and tablet PCs).

If then a user wishes to connect his mobile operator terminal to the medical device, he photographs the displayed code with the existing camera and the App decodes the information contained therein. Filming (instead of photographing) of the code could also be relevant if the code is not static but varying with time and represents a sequence of a number of code pages (code sequence) in order to transport more information than is possible, e.g., with a static QR code (quick response code) or bar code. It would also be possible to film a flickering of an LED mounted on the device (could even be an infrared LED). Modern mobile phone cameras are sensitive in the IR range and it would be possible to copy the principle of infrared remote control in this case—however with a slower code sequence since the cameras operate with a lower sampling rate than an infrared transmitter of a remote control.

If the user has a mobile operator terminal without camera, the following approach can also be chosen as an alternative to displaying the matrix code and photographing the code: instead of an optical code on the monitor, the medical device reproduces the necessary log-in data as coded (inaudible) audio signal or as sound waves in the range between −17 and −20 kHz via the loudspeakers, present as a rule, of the medical device. During the log-in attempt, the mobile operator terminal correspondingly activates its microphone and decodes the received audio signals and thus receives the necessary log-in data.

Other technical alternatives to conveying a code are also conceivable. It would be possible, e.g., to selectively influence the magnetic sensors (el. compass) installed in current Smartphones/tablets by selective influencing of electromagnets (which are installed in the system) and, by means of dedicated application software (e.g. App of the medical device manufacturer) which runs on the mobile device, to selectively detect these changes in modulation (e.g. amplitude fluctuations) in the magnetic sensor and decode a signal therefrom. Although it will as a rule only be possible here to transmit a few bytes meaningfully, this is already sufficient for a first pairing.

In the next step, the App of the mobile operator terminal sets up a data connection to the medical device (HMI server) with the log-in data obtained. The App in this process conveys specifics of the mobile operator terminal (screen size and resolution, screen aspect ratio, type of existing input capability, speed of the data connection . . . ) and its own version identifier.

The HMI server thereupon decides, using the parameters obtained, whether linking the mobile operator terminal is generally possible or whether, e.g., the version of the client used or the screen size are not compatible.

If there is a basic compatibility, the HMI server selects in accordance with the given framework conditions one of a number of predefined GUI formats ("GUI templates", e.g. for small Smartphone screens having a reduced number of controls, large tablet screens, screens in a portrait or landscape format, laptops with mouse operation instead of multitouch . . . ) and begins with the streaming of the suitable GUI version and the reception of the operating information. The unknown mobile operator terminal is thus then linked to the medical device.

Figure 2:
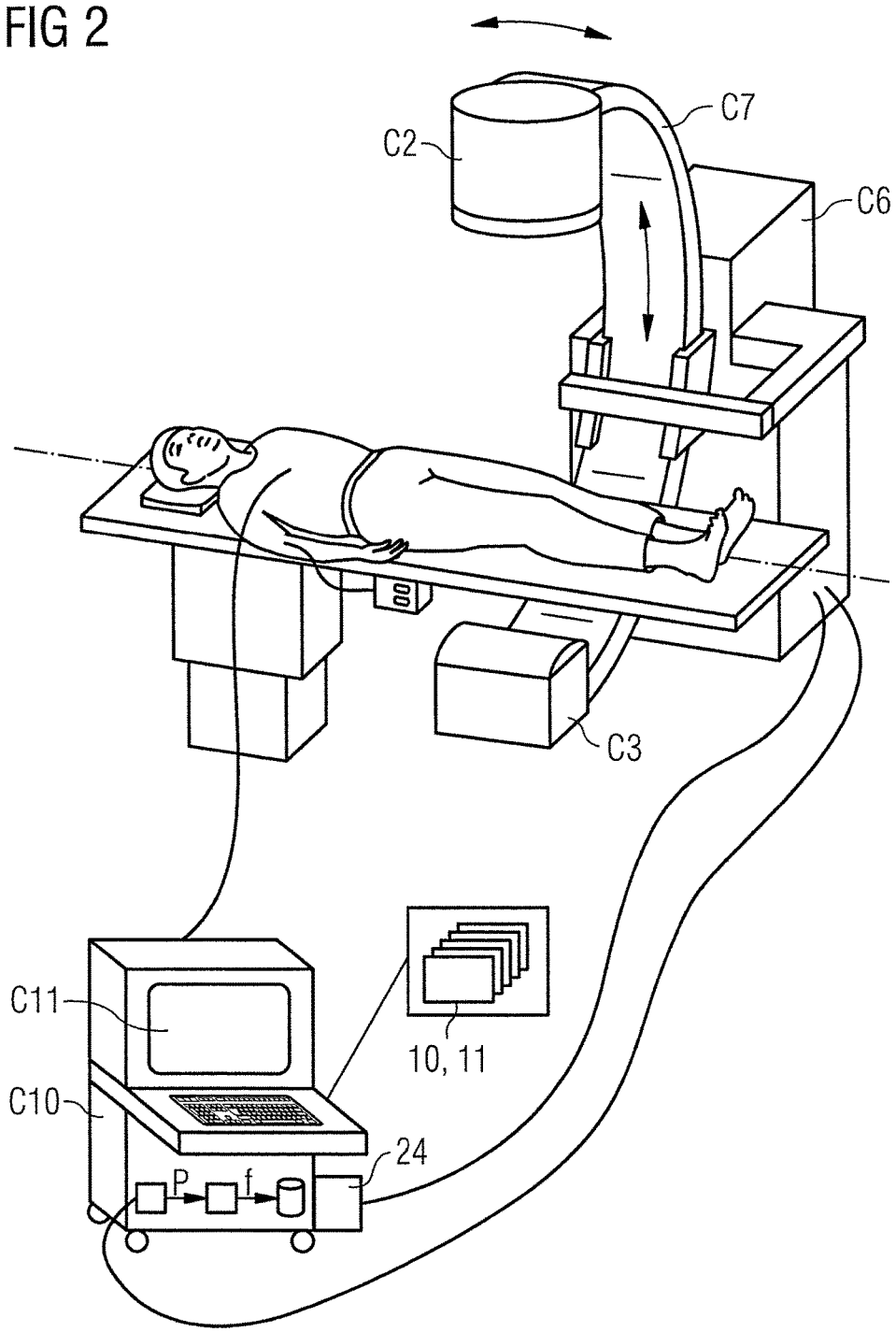
FIG. 2 shows a C arch with associated operator consolee

FIG. 2 shows an example of a medical device for which the invention can be used. This is a C-arch system in which a housing C6 carries the C-arch C7 on which, on the one hand, the X-ray tube C2 and, on the other hand, the opposite detector C3 are mounted. One part of the C-arch system is an operator console C10 which contains the control software required for controlling the C-arch, the system controller 10. In addition, it is equipped with an HMI server 11 and has a screen C11. Thus, the invention can also be used in such a constellation. An operating person has the option of using, instead of the operator console C10, their own mobile operator terminal in that the mobile operator terminal performs a pairing according to the invention with the operator console belonging to the C-arch system. The screen C11 of the operator console would then be used for outputting an optical code. Within the framework of the nomenclature used in this application, the operator console C11 represents a stationary operating unit although it is spatially movable within a certain framework.

In the course of the present application, each operating unit is considered to be stationary with respect to a device to be controlled by this means which comprises means necessary for controlling the device (control software, as a rule) and, at the same time, is provided dedicated for this special device. Such an operating unit could thus also be integrated in the associated device. This is the case, for example, in the mobile C-arch shown in FIG. 3.

Figure 3:
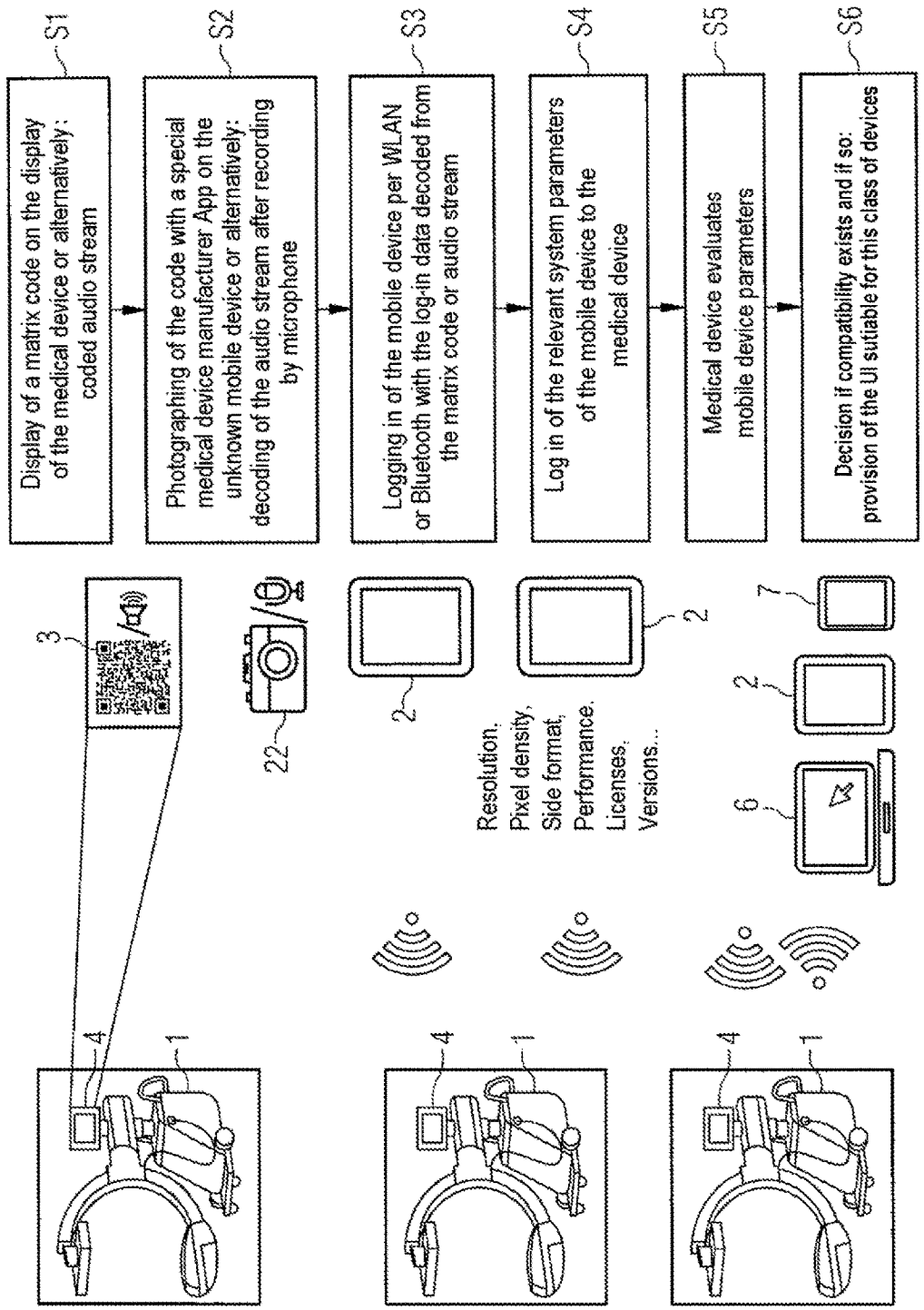
FIG. 3 shows a conceptual image of a link according to the invention to a mobile operator terminal

FIG. 3 shows on the left-hand side elements of the invention and on the right a flowchart for a method according to the invention. A mobile C-arch 1 is shown. This C-arch has a display 4 by which a code 3 can be output. The method comprises the following steps:

S1: A matrix code is displayed on the display 4 of the medical device 1. Alternatively (or possibly also additionally), a coded audio stream is output.

S2: The matrix code is photographed by means of a camera 22 or, respectively, the audio code is recorded by means of a microphone. The mobile operator terminal 2 used comprises a special App by the manufacturer of medical devices by means of which the photographed or recorded code is decoded. Thus, log-in information is extracted from the code.

S3: The mobile operator terminal 2 is logged in by WLAN or Bluetooth with the log-in data decoded from the code.

S4: The relevant system parameters of the mobile operator terminal 2 are reported to the medical device 1. In this context, these can be parameters such as, e.g., resolution, pixel density, side format, performance, licenses, versions (of the operator terminal or the software operated thereon) etc.

S5: The medical device 1 evaluates the reported parameters of the mobile operator terminal 2.

S6: It is decided whether compatibility is present. If this is the case, a GUI suitable for the class of devices used (e.g. tablet computer 2, laptop 6, Smartphone 7) is provided.

Figure 4:
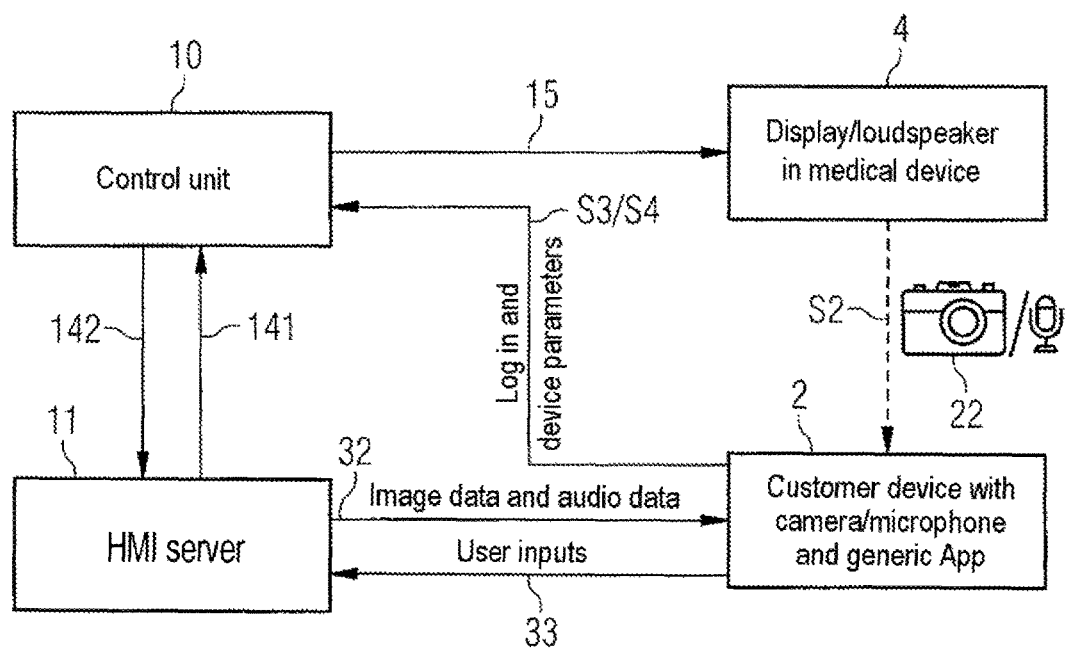
FIG. 4 shows a diagrammatic representation of components involved in the link and of logical data connections

FIG. 4 again shows as block diagram the components involved and logical data connections. A control unit 10 is connected to an HMI server 11. Via an interface, data or control information, respectively, are exchanged in both directions (arrows 141 and 142). The components 10 and 11 correspond to those shown in FIG. 1. A display or loudspeaker 4 is provided for outputting a code (e.g. in the medical device). This code is provided by means of the control unit 10 (arrow 15). The code is conveyed to a customer device or mobile operator terminal 2, respectively. This conveyance corresponds to step S2 from FIG. 3 which is why the arrow symbolizing this step in FIG. 4 was also provided with the reference symbol S2. In this context, a camera 22 is possibly used which is a part of the mobile operator terminal 2. Alternatively, the mobile operator terminal 2 has a microphone for recording an acoustically conveyed code. The mobile operator terminal 2 is provided with a generic App which extracts log-in data from the code for logging in at the medical device. The arrow S3/S4 symbolizes steps S3 and S4 from FIG. 3, i.e. the log-in at the medical device and the transmission of device parameters of the mobile operator terminal 2. Using this information, a connection can be set up between the HMI server 11 and the mobile operator terminal 2 via which image data and audio data are exchanged in one direction (arrow 32) and user inputs in the other direction (arrow 33). This connection or this exchange of data and user inputs, respectively, corresponds to that shown in FIG. 1 which is why the corresponding reference symbols have been used.

The invention has been described in the preceding text for a C-arch or a medical device, respectively. However, it is not restricted to this case. Thus, it can also be used for non-medical devices, e.g. in the field of automation, in the automotive field, in the domestic field etc.

The invention claimed is:

1. A method for connecting a mobile operator terminal to a device to be operated for medical diagnosis or therapy, the method comprising the following steps:
   using an output element associated with the device to output a code, the output element selected from the group consisting of an optical display, a loudspeaker, and an electromagnet;
   optically, acoustically or magnetically conveying the code to the mobile operator terminal;
   using software installed on the mobile operator terminal to decode the conveyed code for determining at least one piece of information related to the device;
   setting up a connection from the mobile operator terminal to a control unit associated with the device with the aid of the at least one piece of information related to the device; and
   conveying at least one piece of information related to the mobile operator terminal, with respect to relevant system parameters of the mobile operator terminal, from the mobile operator terminal to the control unit associated with the device over the set up connection.

2. The method according to claim 1, wherein the at least one piece of information related to the mobile operator terminal, with respect to relevant system parameters of the mobile operator terminal, is information with respect to one or more of the following parameters: availability of a touch screen with a detection of a plurality of fingers, computing power, memory, audio reproducibility, connection bandwidth, licenses, version of the operating terminal, or versions of the software operated thereon.

3. The method according to claim 1, wherein the code contains all required data for a log-in of the mobile operator terminal at the control unit associated with the device.

4. The method according to claim 1, which further comprises carrying out the step of using the output element associated with the device to output the code either following an input of an operator or automatically following a detection of the mobile operator terminal.

5. The method according to claim 1, which further comprises carrying out the step of optically conveying the code to the mobile operator terminal by displaying the code using the output element and recording the displayed code by using a camera of the mobile operator terminal.

6. The method according to claim 1, which further comprises carrying out the step of acoustically conveying the code to the mobile operator terminal using the output element to output the code as an acoustic signal and acoustically conveying the code to the mobile operator terminal.

7. The method according to claim 1, wherein the software installed on the mobile operator terminal being used to decode the code is application software being adapted for the device or a device type associated with the device.

8. The method according to claim 1, which further comprises conveying data required for operation of the device by the mobile operator terminal from the control unit associated with the device to the mobile operator terminal, as determined by the at least one piece of information related to the mobile operator terminal.

9. The method according to claim 1, which further comprises carrying out an assessment of a suitability of the mobile operator terminal for operating the device to be operated, as determined by the at least one piece of information related to the mobile operator terminal and conveyed to the control unit associated with the device.

10. The method according to claim 1, wherein the output element is a monitor, an LED, a microphone or a magnet.

11. A mobile operator terminal configured to be connected to a device to be operated by carrying out the following steps:
    using an output element associated with the device to output a code, the output element selected from the group consisting of an optical display, a loudspeaker, and an electromagnet;
    optically, acoustically or magnetically conveying the code to the mobile operator terminal;
    using software installed on the mobile operator terminal to decode the conveyed code for determining at least one piece of information related to the device;
    setting up a connection from the mobile operator terminal to a control unit associated with the device with the aid of the at least one piece of information related to the device; and conveying at least one piece of information related to the mobile operator terminal, with respect to relevant system parameters of the mobile operator terminal, from the mobile operator terminal to the control unit associated with the device over the set up connection.

12. A device for medical diagnosis or therapy configured to be connected to a mobile operator terminal by carrying out the following steps:

using an output element associated with the device to output a code, the output element selected from the group consisting of an optical display, a loudspeaker, and an electromagnet;

optically, acoustically or magnetically conveying the code to the mobile operator terminal;

using software installed on the mobile operator terminal to decode the conveyed code for determining at least one piece of information related to the device;

setting up a connection from the mobile operator terminal to a control unit associated with the device with the aid of the at least one piece of information related to the device; and conveying at least one piece of information related to the mobile operator terminal, with respect to relevant system parameters of the mobile operator terminal, from the mobile operator terminal to the control unit associated with the device over the set up connection.

13. A system, comprising:

a device according to claim 12; and a mobile operator terminal configured to be connected to said device.

14. The method according to claim 1, wherein the at least one piece of information related to the mobile operator terminal, with respect to relevant system parameters of the mobile operator terminal, is information with respect to one or more of the following parameters: computing power, memory, audio reproducibility, connection bandwidth, licenses, version of the operating terminal, or versions of the software operated thereon.

* * * * *